United States Patent [19]

Lunnen et al.

[11] Patent Number: 5,002,882
[45] Date of Patent: Mar. 26, 1991

[54] METHOD FOR PRODUCING THE XMAI RESTRICTION ENDONUCLEASE AND METHYLASE

[75] Inventors: Keith D. Lunnen, Newbury; Geoffrey G. Wilson, Boxford, both of Mass.

[73] Assignee: New England Biolabs, Inc., Beverly, Mass.

[21] Appl. No.: 344,268

[22] Filed: Apr. 27, 1989

[51] Int. Cl.$^5$ .................. C12N 15/52; C12N 9/22; C12N 1/21
[52] U.S. Cl. .................. 435/172.3; 435/199; 435/252.33; 435/370.1; 536/27; 935/29; 935/73; 935/80; 935/82
[58] Field of Search .................. 435/172.3, 199, 320, 435/252.3, 252.33; 935/29, 73, 80, 82; 536/27

[56] References Cited

FOREIGN PATENT DOCUMENTS 0193413 9/1986 European Pat. Off. .

OTHER PUBLICATIONS

Greene, P. J. et al. (1981), J. Biol. Chem. 256(5), 2143-2153.
Newman, A. K., et al., (1981), J. Biol. Chem. 256(5), 2131-2139.
Schoenef, B. et al., (1983), Gene 24, 227-236.
Walder, R. Y. et al. (1984), J. Biol. Chem. 259(12), 8015-8026.
Endow, S. A. et al. (1977), J. Mol. Biol. 112, 521-529.
Kiss et al. (1985), Nucleic Acids Res. 13, 6403-6421.
Mann et al., Gene 3: 97-112, 1978.
Kosykh et al., Molec. Gen. Genet 178: 717-719, 1980.
Walder et al., Proc. Nat. Acad. Sci. U.S.A., 78: 1503-1507, 1981.
Bougueleret, et al., Nucleic Acids Res. 12: 3659-3676, 1984.
Gingeras and Brooks, Proc. Natl. Acad. Sci., U.S.A. 80: 402-406, 1983.
Theriault and Roy Gene 19: 355-359, 1982.
Blumenthal et al., J. Bacteriol. 164: 501-509, 1985.
Szomolanyi et al., Gene 10: 219-225, 1980.
Janulaitis et al., Gene 20: 197-204, 1982.
Kiss and Baldauf Gene 21: 111-119, 1983.
Walder et al., J. Biol. Chem. 258: 1235-1241, 1983.
Raleigh & Wilson Proc. Natl. Acad. Sci., U.S.A., 83: 9070-9074, 1986.
Qiang and Shildkraut Nucleic Acids Res. 14: 1991-1999, 1986.
Birnboin and Doly, Nucleic Acids Res. 7: 1513, 1979.
Wilson, G. C. (1988), Trends in Genetics 4(11), 314-318.
Lunnen, K. D. et al. (1988), Gene 74, 25-32.
Wilson, G. C. (1988) Gene 74, 286-289.
Borck, K. et al. (1976), Molec. Gen. Genet. 146, 199-207.

*Primary Examiner*—Elizabeth C. Weimar
*Assistant Examiner*—Charles L. Patterson, Jr.
*Attorney, Agent, or Firm*—Gregory D. Williams; David G. Conlin

[57] ABSTRACT

The present invention is directed to a method for cloning and producing the XmaI restriction endonuclease by (1) introducing the restriction endonuclease gene from *X. malvacaerum* into a host whereby the restriction gene is expressed; (2) fermenting the host which contains the plasmid encoding and expressing the XmaI restriction endonuclease activity, and (3) purifying the XmaI restriction endonuclease from the fermented host which contains the plasmid encoding and expressing the XmaI restriction endonuclease activity.

10 Claims, 4 Drawing Sheets

METHOD FOR PRODUCING THE XMAI RESTRICTION ENDONUCLEASE AND METHYLASE

BACKGROUND OF THE INVENTION

The present invention relates to clones for the XmaI restriction endonuclease and modification methylase, and the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria tend to possess at most only a small number restriction endonucleases per species. The endonucleases typically are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The breakup that takes place disables many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (EcoRII: Kosykh et al., Molec. gen. Genet 178: 717–719, (1980); HhaII: Mann et al., Gene 3: 97–112, (1978); PstI: Walder et al., Proc. Nat. Acad. Sci. 78 1503–1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acid. Res. 12: 3659–3676, (1984); PaeR7: Gingeras and Brooks, Proc. Natl. Acad. Sci. USA 80: 402–406, (1983); Theriault and Roy, Gene 19: 355–359, (1982); PvuII: Blumenthal et al., J. Bacteriol. 164: 501–509, (1985)).

A third approach, and one that is being used to clone a growing number of systems, involves selecting for an active methylase gene, see for e.g., BsuRI: Kiss et al., Nucl. Acid. Res. 13: 6403–6421, (1985); and TaqI: Slatko et al., Nucl. Acid. Res. 15: 9781–9796, (1987). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., Gene 10: 219–225, (1980); BcnI: Janulaitis et al, Gene 20: 197–204, (1982); BsuRI: Kiss and Baldauf, Gene 21: 111–119, (1983); and MspI: Walder et al., J. Biol. Chem. 258: 1235–1241, (1983)). For an overall review of cloning restriction-modification systems see for e.g., Lunnen et al, Gene 74: 25–32, (1988); and Wilson, G. G., Gene 74: 281–289, (1988).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease.

Another obstacle to cloning systems in *E. coli* was discovered in the process of cloning diverse methylase genes. Many *E. coli* strains (including those normally used in cloning) have systems that resist the introduction of DNA containing methylated cytosines. (Raleigh and Wilson, Proc. Natl. Acad. Sci., USA 83: 9070–9074, 1986). It is extremely difficult to clone cytosine-specific methylase genes, either alone, or together with their corresponding endonuclease gene, into these strains of *E. coli*. In order to clone these genes, therefore, it is necessary to use mutant strains of *E. coli* in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the XmaI restriction endonuclease and modification methylase derived from *Xanthomonas malvacaerum* (ATCC 9924) (Endow, S. A. and Roberts, R. J., J. Mol. Biol. 112: 521–529, (1977)) as well as related methods for the production of the enzymes. More specifically, this invention relates to clones which express the restriction endonuclease XmaI, an enzyme which recognizes the DNA sequence 5'—CCCGGG—3' and cleaves between $C_1$ and $C_2$ leaving a four nucleotide 5' overhang. See Endow et al., supra, the disclosure of which is hereby incorporated by reference herein. XmaI restriction endonuclease produced in accordance with the present invention is substantially pure and free of the contaminants normally found in XmaI preparations made by conventional techniques.

The preferred method for cloning the genes for the XmaI enzymes comprises forming a library containing the DNA from *X. malvacaerum*, isolating those clones which contain DNA coding for the XmaI modification methylase and screening among these to identify those that also contain the XmaI restriction endonuclease gene.

DETAILED DESCRIPTION OF THE INVENTION

The present invention relates to clones of the XmaI restriction and modification genes, as well to the restriction endonuclease XmaI produced from such clones. The XmaI genes are preferably cloned by a method which takes advantage of the fact that certain clones which are selected on the basis of containing and expressing the XmaI modification methylase gene also contain the XmaI restriction gene. The DNA of such clones is resistant to digestion, in vitro, by the XmaI restriction endonuclease as well as the SmaI restriction endonuclease. (The SmaI restriction endonuclease is an isoschizomer of XmaI.) This resistance to digestion affords a means for selectively isolating clones encoding the XmaI methylase and restriction endonuclease.

Figure 1:
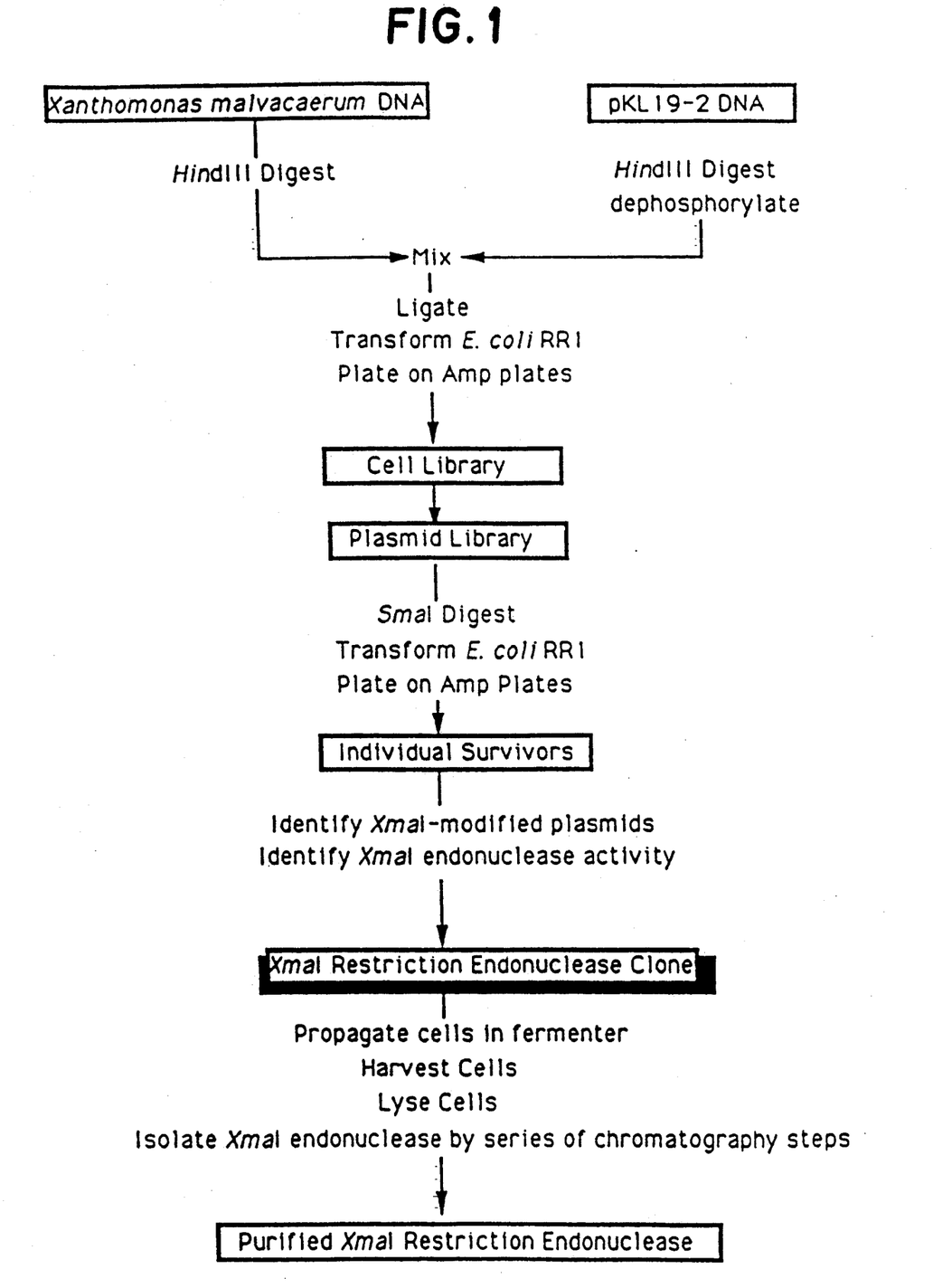
FIG. 1 illustrates the scheme for cloning and producing the XmaI restriction endonuclease.
Figure 2:
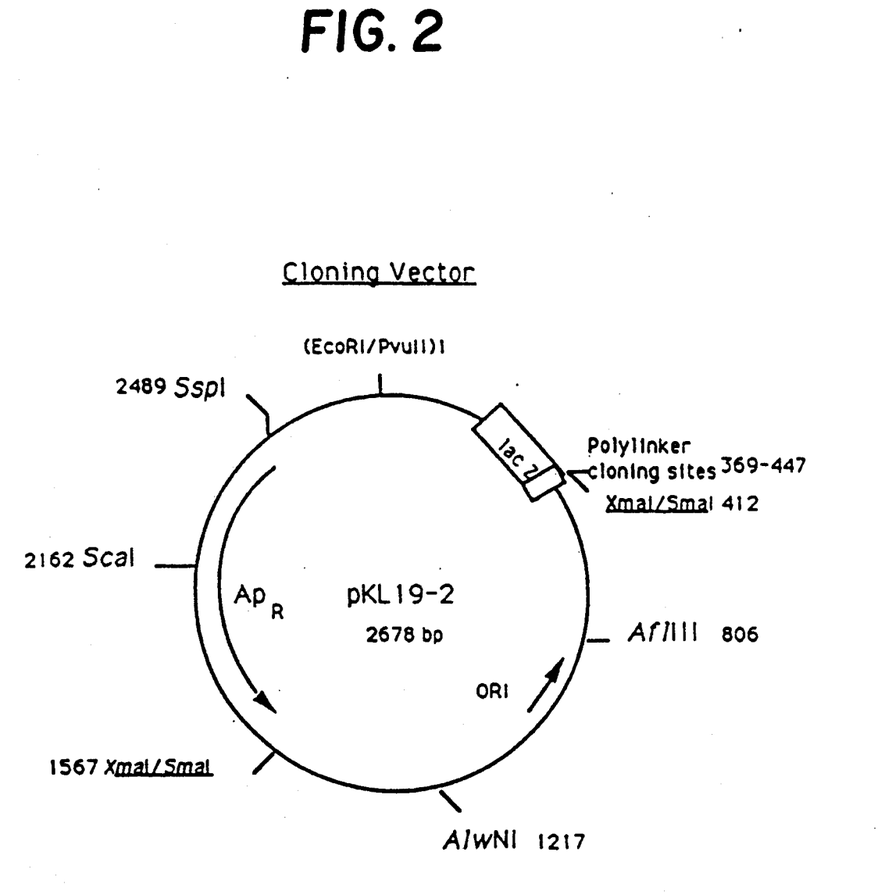
FIG. 2 is a restriction map of the pUC19 cloning vector derivative pKL19-2 which contains a second XmaI/SmaI site.

The method described herein by which the XmaI restriction gene and methylase gene are preferably cloned and expressed are illustrated in FIG. 1, and they include the following steps:

1. The growth and lysis of *X. malvacaerum*. (ATCC 9924). *X. malvacaerum* is grown and lysed in accordance with techniques described by Endow et al.

2. The DNA of *X. malvacaerum* is purified by standard techniques such as, phenol and chloroform extraction, dialysis, and isopropanol precipitation.

3. The DNA is digested partially with either of the restriction endonucleases HindIII, BamHI and EcoRI.

4. The digested DNA is ligated into a cloning vector, such as a pBR322 derivative containing a BamHI, HindIII or EcoRI site. XmaI clones were obtained using pKL19-2 as the cloning vector. pKL19-2 is pUC19 to which a second XmaI/SmaI site was inserted, replacing the DNA between DraI sites at nucleotides 1563 and 1582, using an 8-bp phosphorylated linker, d(pCCCCGGGG). (A sample of pKL19-2 is desposited in the ATCC under ATCC number 67977). The resulting mixture is used to transform an appropriate host such as *E. coli* strain RR1 (ATCC 31343).

5. The DNA/cell mixture is plated on antibiotic media selective for transformed cells, such as ampicillin. After incubation, the transformed cell colonies are collected together into a single culture, the primary cell library.

6. The recombinant plasmids are purified in toto from the primary cell library to make a primary plasmid library.

7. The plasmid library is then digested to completion in vitro with the SmaI restriction endonuclease, which was prepared from *Serratia marcescens* cells (Endow et al.) by standard protein purification techniques such as affinity-chromatography and ion-exchange chromatography. XmaI-methylated DNA is resistant to digestion by both XmaI and SmaI restriction endonucleases. Digestion causes the selective destruction of unmodified, non-methylase-containing clones, resulting in an increase in the relative frequency of XmaI methylase-carrying clones. SmaI restriction endonuclease recognizes the same sequence as XmaI, but cuts between $C_3$ and $G_1$ in the sequence 5'—CCCGGG—3' leaving blunt ends. Cleaved, blunt-ended molecules are less likely to resume circularity upon transformation; SmaI digestion of the primary library is therefore probably more selective for modified molecules than is XmaI digestion.

8. The digested plasmid library DNA is transformed back into an appropriate host, such as *E. coli* strain RR1, and transformed colonies are again obtained by plating on antibiotic plates. The colonies are picked and their DNA is analyzed for the presence of the XmaI modification gene in the following manner: The plasmid DNA that they carry is purified and incubated in vitro with XmaI restriction endonuclease to determine whether it is resistant to digestion by XmaI. The total cellular DNA (chromosomal and plasmid) of the clone is also purified and incubated with XmaI restriction endonuclease. The DNA of clones that carry the XmaI methylase gene should be modified, and both the plasmid DNA and the total DNA should be found to be substantially, or completely resistant to digestion.

9. Clones carrying the XmaI restriction endonuclease are identified by preparing crude extracts of those clones identified in step 8 as carrying the XmaI methylase gene, and assaying the extracts for XmaI restriction endonuclease activity.

10. The XmaI restriction endonuclease may be produced from clones carrying the XmaI restriction and modification genes by propagation in a fermenter in a rich medium containing ampicillin. The cells are thereafter harvested by centrifugation and disrupted by sonication to produce a crude cell extract containing the XmaI restriction endonuclease activity.

11. The crude cell extract containing the XmaI restriction endonuclease activity is purified by standard protein purification techniques such as affinity-chromatography, and ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of XmaI Restriction Endonuclease Gene

1. DNA purification: To prepare the DNA of *Xanthomonas malvacaerum* (ATCC 9924), 5 g of frozen cells were thawed 1 hour on ice in 20 ml of 25% sucrose, 50 mM Tris, pH 8.0 10 ml of 0.25M EDTA, pH 8 was added plus 6 ml 10 mg/ml lysozyme in 0.25M Tris, pH 8.0. The suspension was incubated on ice 2 hours. To achieve cell lysis, 24 ml of lysis mix (1% Triton X-100, 50 mM Tris, 62 mM EDTA pH 5.0) and 5 ml 10% SDS were added. The sample was extracted with 70 ml of phenol, (previously equilibrated with 0.5M Tris pH 8.0), and then with 60 ml of Chloroform. The emulsion was centrifuged at 10k rpm for 30 minutes. The viscous upper layer was withdrawn and dialyzed for 24 hours against 10 mM Tris, 1 mM EDTA, pH 8.0 (four buffer changes, 4 liters each). The dialyzed solution was then digested with RNase at a final concentration of 100 microgram/ml for 1 hour at 37° C. The DNA was then harvested by adding NaCl to a final concentration of 0.4M, overlaying with 0.55 volumes of isopropyl alcohol, and spooling DNA onto a glass rod by mixing the phases together. The DNA was resuspended in 10 mM Tris, 1 mM EDTA, pH 8.0 and stored at 4° C.

2. Digestion of DNA: The purified DNA was cleaved partially with HindIII. DNA was diluted to a concentration of 100 micrograms per ml in 50 mM Tris pH 7.5, 100 mM NaCl, 10 mM MgCl$_2$, 10 mM 2-mercaptoethanol, and 4.0 units of HindIII per microgram of DNA was added to a first tube and then transferred to a second tube to achieve 2.0 units of HindIII/ug and so on, each succeeding tube receiving half of the previous amount of enzyme. The DNA was digested for one hour at 37° C., then the digestions were terminated by heating to 72° C. for 10 minutes. Tubes exhibiting moderate, but incomplete digestion were chosen as the source of partial digest fragments for cloning. (These were the 0.5 u/ug, 0.25 u/ug, 0.1 u/ug, 0.05 u/ug, and 0.02 u/ug tubes. The five solutions were mixed together and used as described below.)

3. Ligation: The digested DNA was ligated to pKL19-2 as follows: 6.0 ug of HindIII-digested *X. malvacaerum* DNA (60 ul) was mixed with 3.0 ug of HindIII-cleaved and dephosphorylated pKL19-2 (7.5 ul). 20 ul of 10X ligation mix (500 mM Tris, pH 7.5, 100 mM MgCl$_2$, 100 mM DTT, 5 mM ATP) was added, plus 112.5 ul of sterile distilled water to bring the final volume to 200 ul. 7.5 ul of T4 DNA ligase was added and the mixture was incubated at 17° C. for 4 hours, then sterilized by the addition of 10 ul of chloroform. Approximately 125 ul of the ligated DNA was used to transform *E. coli* strain RR1 as follows: The DNA was mixed with 1.0 ml of SSC/CaCl$_2$ (50 mM NaCl, 5 mM Na$_3$ Citrate, 67 mM CaCl$_2$) on ice and 2.0 ml of ice-cold competent *E. coli* RR1 (hsd R$^-$M$^-$, ATCC No. 31343) cells were added. After a 5-minute incubation at 42° C., the cells were diluted by the addition of 8 ml of Luria-broth (L-broth) then incubated at 37° C. for 4 hours.

4. Primary Cell Library: The transformed cell culture was briefly centrifuged, the supernatant was discarded and the cells were resuspended in 1.0 ml of L-broth. 200 ul portions were plated onto Luria-agar (L-agar) plates containing 100 ug/ml ampicillin. After overnight incubation at 37° C., the plates were each flooded with 2.5 ml of 10 mM Tris, pH 7.5, 10 mM MgCl$_2$ and the transformed colonies were scraped together and pooled to form the primary cell library.

5. Primary Plasmid Library: The primary plasmid library was prepared as follows: 2.5 ml of the primary cell library was inoculated into 500 ml of L-broth containing 100 ug/ml ampicillin. The culture was shaken overnight at 37° C. then centrifuged at 4000 rpm for 5 minutes. The supernatant was discarded and the cell pellet was resuspended in 10 ml of 25% sucrose, 50 mM Tris, pH 8.0, at room temperature. 5 ml of 0.25M EDTA, pH 8.0, was added, followed by 3 ml of 10 mg/ml lysozyme in 0.25M Tris, pH 8.0. The solution was left on ice for 1 hour, then 12 ml of lytic mix (1% Triton X-100, 50 mM Tris, pH 8.0, 67 mM EDTA) was forcefully pipetted in, and the cell suspension was gently swirled to achieve lysis. After lysis, the mixture was transferred to a 50 ml plastic centrifuge tube and spun at 17000 rpm, 4° C. for 45 minutes. The supernatant was removed with a pipette. 20.0 g of solid CsCl was weighed into a 50 ml plastic screw-cap tube and 22.0 g of supernatant was pipetted into the tube and mixed. 1.0 ml of ethidium bromide solution (5 mg/ml ethidium bromide in 10 mM Tris, pH 8.0, 1 mM EDTA, 100 mM NaCl) was added to the mixture. The solution was transferred to two 5/8 in. ×3 in. polyallomer centrifuge tubes and sealed. These tubes were then spun in a Beckman Ti70 rotor for 42 hours at 44000 rpm, 17° C. To collect the plasmids, the tubes were illuminated with ultraviolet light, the tops were pierced with a scalpel and the lower of the two fluorescent DNA bands was collected by syringe. The lower band from each tube was combined into a screw-top glass tube and the ethidium bromide was removed by extracting 4 times with an equal volume of water-saturated ice-cold N-Butanol.

The extracted solution was transferred to dialysis tubing and dialyzed for 24 hours against 4 changes of DNA buffer (10 mM Tris pH 7.5, 1 mM EDTA). The dialyzed DNA solution was then transferred to a preweighed 50 ml sterile centrifuge tube and its volume was measured. 5M NaCl was added to a final concentration of 0.4M, then 2 volumes of isopropanol were added and mixed. The solution was stored overnight at −20° C. to precipitate the DNA. After precipitation, the solution was spun at 15000 rpm, 0° C. for 15 minutes and the supernatant was discarded. The tube was left on the bench to air-dry for 15 minutes, then the DNA pellet was dissolved in 500 ul of DNA buffer and stored at −20° C. The DNA concentration of plasmid libraries prepared in this way was found to be 100 to 200 ug/ml.

6. Digestion of Plasmid Pool: The primary plasmid pool was digested to destroy non-XmaI methylase clones as follows: 0.5 ug of the plasmid library in 90 ul of SmaI-digestion buffer (6 mM Tris.HCl, pH 8.0, 6 mM $MgCl_2$, 6 mM 2-mercaptoethanol, 20 mM KCl) was incubated with 20 units (2 ul) of SmaI restriction enzyme at 25° C. for 2 h. The digested DNA was chloroform-extracted and microfuged.

7. Transformation: A 12.5 ul sample from the tube was used to transform 200 ul of competent E. coli RR1. The cell/DNA mixtures were plated onto L-agar plates containing 100 ug/ml ampicillin. After overnight incubation at 37° C., the plates were examined. Digestion of the plasmid library with SmaI was found to have reduced the number of transformants by a factor greater than $10^4$. Individual colonies were picked from the plate and each was inoculated into 10 ml of L-broth containing ampicillin, to prepare a miniculture, and was also streaked onto L-agar plates containing ampicillin to prepare a master stock.

8. Analysis of surviving individuals: Twenty-nine of the surviving colonies obtained from section 8 were grown up into 10 ml cultures (section 7) and the plasmids that they carried were prepared by the following miniprep purification procedure, adapted from the method of Birnboim and Doly (Nucleic Acids Res. 7: 1513, (1979)).

Miniprep Procedure

Each culture was centrifuged at 8000 rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5 ml of 3M sodium acetate, pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes. Once dry, the pellets were resuspended in 850 ul of 10 mM Tris, 1 mM EDTA, pH 8.0. 75 ul of 5M NaCl was added to each and the solutions were transferred to Eppendorf tubes containing 575 ul of isopropanol, and again precipitated for 10 minutes at room temperature. The tubes were then spun for 45 seconds in a microfuge, the supernatants were discarded and the pellets were air-dried. The pellets were then dissolved in 500 ul of 10 mM Tris, 1 mM EDTA, pH 8.0, containing 100 ug/ml RNase and incubated for 1 hour at 37° C. to digest the RNA. The DNA was precipitated once more by the addition of 50 ul of 5M NaCl followed by 350 ul of isopropanol. After 10 minutes at room temperature, the DNA was spun down by centrifugation for 45 seconds, the supernatants were discarded and the pellets were redissolved in a final solution of 150 ul of 10 mM Tris 1 mM EDTA, pH 8.0. The plasmid minipreps were subsequently analyzed by digestion with XmaI.

Figure 3:
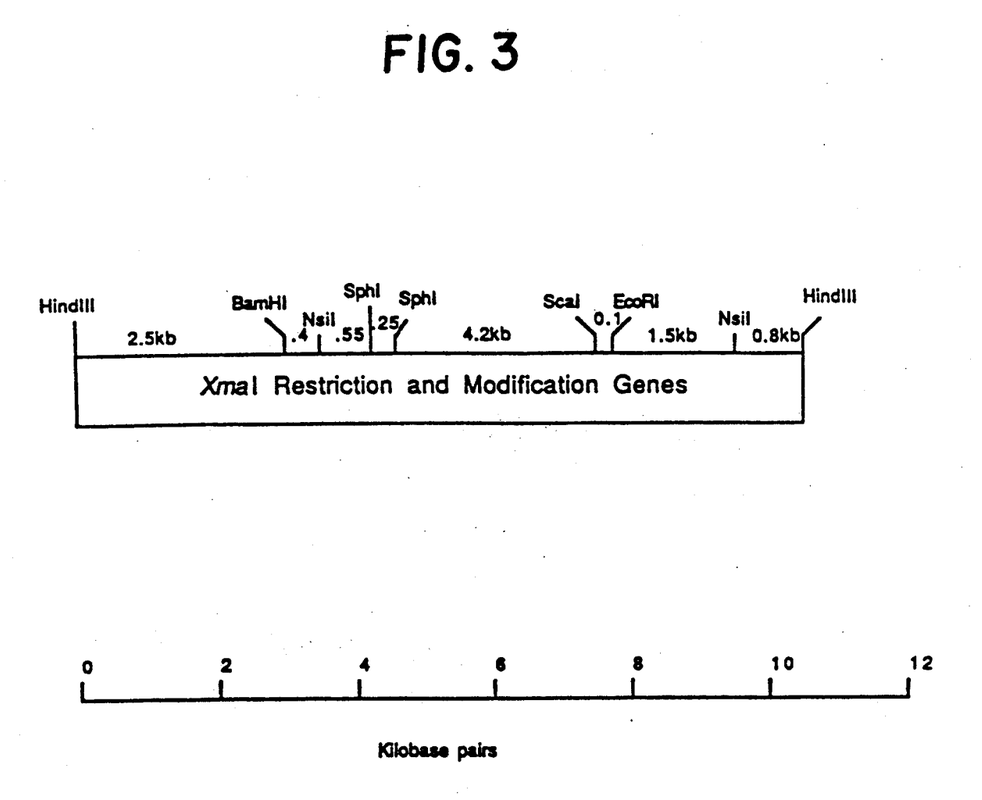
FIG. 3 is a restriction map of a 10.3 kb HindIII fragment insert encoding the XmaI restriction endonuclease and modification methylase.

9. XmaI Methylase Gene Clones: Seventeen of the plasmids that were analyzed were found to be fully resistant to digestion by the XmaI restriction enzyme. The clones carried one HindIII fragment of approximately 10.3 kb in length. (See FIG. 3). These plasmids appeared to be identical and were subsequently shown to carry not only the XmaI modification methylase gene but also the XmaI restriction endonuclease gene.

10. XmaI Restriction Gene Clone: One of the plasmids, designated pKLXmaIRM 102-2, identified above (section 9) as carrying the XmaI modification methylase gene was also found to carry the XmaI restriction endonuclease gene. This was established by an in vitro restriction endonuclease assay of an extract prepared from E. coli strain K802 (ATCC 33526) into which the plasmid has been transferred by transformation.

A sample of pKLXmaIRM102-2 has been deposited at the American Type Culture Collection under ATCC Accession No. 40873.

Endonuclease Assays

To assay for endonuclease activity, two solutions were prepared:
(i) 10X restriction endonuclease buffer: 100 mM Tris, pH 7.5, 100 mM MgC12, 100 mM 2-mercaptoethanol, 500 mM NaCl; and (ii) digestion reaction mix: 55 ul HindIII-digested Lambda DNA (500 ug/ml), 55 ul 10X restriction endonuclease buffer, 440 ul distilled water to achieve 50 ug/ml DNA.

Figure 4:
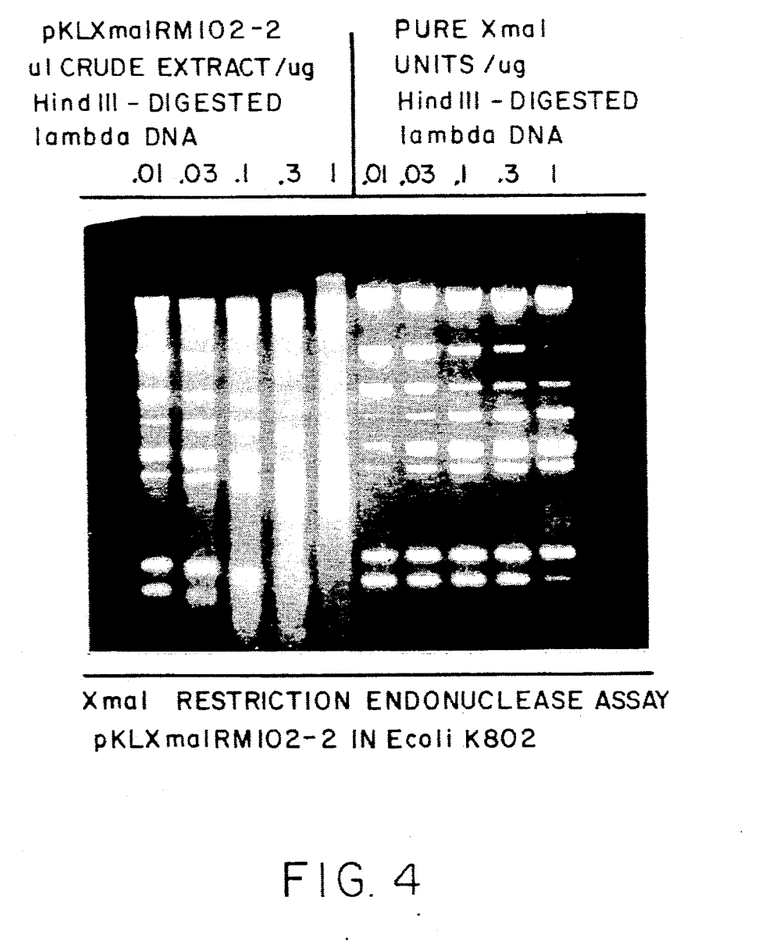
FIG. 4 is a photograph of an agarose gel illustrating XmaI restriction endonuclease activity obtained from the crude extract of pKLXmaIRM 102-2.

The cell extract was prepared as follows: A 100 ml culture of the clone was grown overnight in L-broth plus 100 ug/ml ampicillin at 37° C. and the cells were pelleted by centrifugation at 4000 rpm for 5 minutes. The supernatant was discarded and the pellet was resuspended in 3 ml of sonication buffer (50 mM $KPO_4$ pH 7.5, 10 mM BME, 0.1 mM EDTA). 0.3 ml of sonication buffer containing 10 mg/ml lysozyme was added, the suspension was swirled and then left on ice for 1 hour. A 1 ml sample was transferred to an Eppendorf tube and sonicated gently for three 10-second bursts to disrupt the cells. The tube was spun for 5 minutes in a microfuge and the supernatant was used as the cell extract. To assay the extract, the digestion reaction mix was dispensed into 5 tubes, 150 ul into the first tube and 100 ul into each of the remaining 4 tubes. 7.5 ul of the extract was added to the first tube and mixed. 47.5 ul was removed from the first tube and transferred to the second tube, mixed and so on. The first tube thus received 1.0 ul of extract per ug of DNA, the second tube 0.3 ul/ug, the third tube, 0.1 ul/ug and so on. The tubes, each now containing 100 ul, were incubated at 37° C. for one hour, then a 20 ul sample of each was analyzed by gel electrophoresis. The titre of the extract was found to be approximately $1\times 10^3$ units per ml, which corresponds to about 1 to $2\times 10^5$ units of XmaI restriction endonuclease per gram of cells. (See FIG. 4).

What is claimed is:
1. Isolated DNA coding for the XmaI restriction endonuclease, wherein the isolated DNA is obtainable from the vector pKLXmaIRM102-2.

2. A recombinant DNA vector comprising a vector into which a DNA segment coding for the XmaI endonuclease produced by *Xanthomonas malvacaerum* ATCC No. 9924 has been inserted.

3. Isolated DNA coding for the XmaI restriction endonuclease and methylase, wherein the isolated DNA is obtainable from the vector pKLXmaIRM102-2.

4. A cloning vector comprising the isolated DNA of claim 1.

5. A cloning vector comprising the isolated DNA of claim 3.

6. The cloning vector of claim 5, wherein the cloning vector comprises pKLXmaIRM102-2.

7. A host cell transformed by the vector of claim 4, 5 or 6.

8. A method of cloning DNA coding for an XmaI restriction endonuclease comprising:

(a) purifying DNA from *Xanthomonas malvacaerum* ATCC No. 9924;

(b) partially digesting the purified DNA with HindIII to form DNA fragments;

(c) ligating the DNA fragments into the cloning vector pKL-19-2;

(d) transforming a host cell with the cloning vector of step (c) to form a cell library; and (e) purifying recombinant vectors from the cell library to form a plasmid library;

(f) contacting the plasmid library of step (e) with SmaI to form a digestion pool, transforming the digestion pool into a host cell, and screening for the presence of one or more cloning vectors containing DNA coding for an XmaI methylase;

(g) screening the cloning vector of step (f) which contains DNA coding for XmaI methylase for the presence of DNA coding for an XmaI restriction endonuclease by contacting the cloning vector with SmaI; and (h) isolating the cloning vector of step (g) which contains DNA coding for XmaI restriction endonuclease.

9. A method of producing XmaI restriction endonuclease comprising culturing a host cell transformed with the vector of claim 4, 5 or 6 under conditions suitable for the expression of said endonuclease.

10. A method for producing XmaI restriction endonuclease:

(a) purifying DNA from *Xanthomonas malvacaerum* ATCC No. 9924;

(b) partially digesting the purified DNA with HindIII to form DNA fragments;

(c) ligating the DNA fragments into the cloning vector pKL-19-2;

(d) transforming a host cell with the cloning vector of step (c) to form a cell library; and (e) purifying recombinant vectors from the cell library to form a plasmid library;

(f) contacting the plasmid library of step (e) with SmaI to form a digestion pool, transforming the digestion pool into a host cell, and screening for the presence of one or more cloning vectors containing DNA coding for an XmaI methylase;

(g) screening the cloning vector of step (f) which contains DNA coding for XmaI methylase for the presence of DNA coding for an XmaI restriction endonuclease by contacting the cloning vector with SmaI;

(h) isolating the cloning vector of step (g) which contains DNA coding for XmaI restriction endonuclease; and (i) culturing a host cell transformed with the cloning vector of step (h) under conditions suitable for expression of XmaI restriction endonuclease.

* * * * *

UNITED STATES PATENT AND TRADEMARK OFFICE
CERTIFICATE OF CORRECTION

PATENT NO. : 5,002,882

DATED : March 26, 1991

INVENTOR(S) : Lunnen, et al.

It is certified that error appears in the above-identified patent and that said Letters Patent is hereby corrected as shown below:

Col. 4, line 30 "ATCC 67977" should be --67997--.

Signed and Sealed this

Sixteenth Day of March, 1993

Attest:

STEPHEN G. KUNIN

Attesting Officer

Acting Commissioner of Patents and Trademarks